United States Patent

(12)
Coffeng

(10) Patent No.: US 12,419,529 B2
(45) Date of Patent: Sep. 23, 2025

(54) NONINVASIVE BLOOD PRESSURE MONITORING SYSTEM AND METHOD

(71) Applicant: GE Precision Healthcare LLC, Wauwatosa, WI (US)

(72) Inventor: Rene Coffeng, Helsinki (FI)

(73) Assignee: GE Precision Healthcare LLC, Wauwatosa, WI (US)

( * ) Notice: Subject to any disclaimer, the term of this patent is extended or adjusted under 35 U.S.C. 154(b) by 1048 days.

(21) Appl. No.: 17/353,194

(22) Filed: Jun. 21, 2021

(65) Prior Publication Data

US 2022/0400967 A1    Dec. 22, 2022

(51) Int. Cl.
| | |
|---|---|
| A61B 5/0225 | (2006.01) |
| A61B 5/0205 | (2006.01) |
| A61B 5/024 | (2006.01) |
| A61B 5/025 | (2006.01) |
| A61B 5/0531 | (2021.01) |
| A61B 5/352 | (2021.01) |

(52) U.S. Cl.
CPC ........ A61B 5/02255 (2013.01); A61B 5/0205 (2013.01); A61B 5/02405 (2013.01); A61B 5/025 (2013.01); A61B 5/0531 (2013.01); A61B 5/352 (2021.01); A61B 2562/0247 (2013.01)

(58) Field of Classification Search
None
See application file for complete search history.

(56) References Cited

U.S. PATENT DOCUMENTS

| | | | |
|---|---|---|---|
| 4,349,034 A | | 9/1982 | Ramsey, III |
| 4,543,962 A | * | 10/1985 | Medero .................. A61B 5/022 600/495 |
| 4,917,116 A | * | 4/1990 | La Viola ................ A61B 5/022 600/494 |
| 5,215,096 A | * | 6/1993 | Zapf .................. A61B 5/02225 600/495 |
| 5,404,878 A | | 4/1995 | Frankenreiter et al. |
| 5,865,756 A | | 2/1999 | Peel, III |
| 6,423,010 B1 | | 7/2002 | Friedman et al. |
| 8,211,030 B2 | | 7/2012 | Donehoo et al. |
| 10,881,314 B2 | | 1/2021 | Muuranto et al. |
| 10,959,616 B2 | | 3/2021 | Karru et al. |
| 2006/0142968 A1 | * | 6/2006 | Han ..................... A61B 5/4809 702/120 |

(Continued)

FOREIGN PATENT DOCUMENTS

| | | |
|---|---|---|
| EP | 0895748 A3 | 3/2000 |
| EP | 0960598 B1 | 7/2008 |

*Primary Examiner* — Jacqueline Cheng
*Assistant Examiner* — Samuel C Kim
(74) *Attorney, Agent, or Firm* — Andrus Intellectual Property Law, LLP

(57) ABSTRACT

A method of measuring noninvasive blood pressure includes determining a window for pulse detection for a patient, receiving a pressure signal measured from a measure sensor in a blood pressure cuff, and setting a pulse detection period for each heart beat based on the window and a heart beat indicator indicating at least one heart beat time for the patient. The pressure signal is then examined within each pulse detection period to identify a pressure peak therein. A blood pressure for the patient is determined based on the pressure peaks detected in the pressure signal.

19 Claims, 7 Drawing Sheets

(56) References Cited

U.S. PATENT DOCUMENTS

| | | | |
|---|---|---|---|
| 2007/0208258 A1* | 9/2007 | Whitaker | A61B 5/021 |
| | | | 600/490 |
| 2008/0045846 A1* | 2/2008 | Friedman | A61B 5/02255 |
| | | | 600/490 |
| 2012/0283583 A1 | 11/2012 | Batkin et al. | |
| 2014/0180144 A1* | 6/2014 | Chen | A61B 5/02225 |
| | | | 600/494 |
| 2019/0104947 A1* | 4/2019 | Shigemori | A61B 5/352 |
| 2023/0225624 A1* | 7/2023 | Sola i Caros | A61B 5/7221 |
| | | | 600/480 |

* cited by examiner

NONINVASIVE BLOOD PRESSURE MONITORING SYSTEM AND METHOD

BACKGROUND

The present disclosure generally relates to methods and systems for non-invasively measuring blood pressure. More specifically, the present disclosure relates to a non-invasive blood pressure (NIBP) monitor and measurement control method that provides improved pressure pulse detection.

The oscillometric method of measuring blood pressure involves applying an inflatable cuff around an extremity of a patient's body, such as a patient's upper arm. The cuff is then inflated to a pressure above the patient's systolic pressure and then incrementally reduced in a series of small steps. A pressure sensor measures the cuff pressure at each step. The sensitivity of the sensor is such that pressure fluctuations within the artery resulting from the beats of the patient's pulse may be detected. These pulses are transferred to the inflated cuff causing slight pressure variations within the cuff which are detected by a pressure sensor. The pressure sensor produces an electrical signal, referred to herein as a pressure signal, which typically comprises a DC component representing the incremental cuff pressure and a series of small periodic variations associated with the beats of the patient's pulse. These small variations in the pressure signal are often referred to as "oscillation complexes," or simply "oscillations."

A patient's blood pressure may be estimated based on an analysis of these oscillation complexes. After filtering out the DC component and amplifying the signal generated by the cuff pressure sensor, peak pulse amplitudes (PPA) may be determined for each oscillometric complex. The PPA will tend to increase as the cuff pressure is reduced until a peak amplitude is reached. Once this peak has been reached, the PPA will begin to decrease with further reductions in cuff pressure. The peak pulse amplitudes thus form an oscillometric blood pressure envelope for the patient. The cuff pressure at which the oscillations have a maximum value has been found to be representative of the patient's mean arterial pressure (MAP). The systolic and diastolic pressures can be derived either as predetermined fractions of MAP, or by more sophisticated estimating techniques using direct processing of the oscillation complexes.

The presence of an arrhythmia or other cardiac abnormality can affect blood pressure measurements using the oscillometric method. Namely, any abnormality or cardiac event that causes irregular heart beats or irregular stroke volumes pose challenges for detecting the PPAs. The prior art recognizes the problems associated with calculating blood pressure in the presence of artifacts and arrhythmias, which has been a long-standing problem faced in the relevant art of noninvasive blood pressure monitoring. U.S. Pat. No. 6,423,010 recognizes several prior art methods and systems for addressing arrhythmias.

Automated blood pressure monitoring has rapidly become an accepted and central aspect of human health care. Such monitors are now a conventional part of patient monitoring, especially in emergency rooms, intensive and critical care units, and in the operating room. Traditionally, NIBP monitoring devices have been connected to sensors through cables and/or tubing. However, such cables and or tubing can be problematic because they inhibit patient movement and create obstacles to clinicians engaged in patient care. Thus, there has been a push towards wireless patient monitoring.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, a method of measuring noninvasive blood pressure includes determining a window for pulse detection for a patient, receiving a pressure signal measured from a measure sensor in a blood pressure cuff, and setting a pulse detection period for each heart beat based on the window and a heart beat indicator indicating at least one heart beat time for the patient. The pressure signal is then examined within each pulse detection period to identify a pressure peak therein. A blood pressure for the patient is determined based on the pressure peaks detected in the pressure signal.

An exemplary method of measuring non-invasive blood pressure using a blood pressure cuff includes receiving an average heart rate and/or an RR interval variability for a patient and then calculating a window for pulse detections based on the average heart rate and/or the RR interval variability. A pressure signal measured from a pressure sensor in the blood pressure cuff is received and a heart beat indicator indicating heart beat times for the patient is also received. The blood pressure cuff is deflated in a series of pressure steps. At each pressure step, a first pulse detection period is set based on the window and a first heart beat time indicated by the heart beat indicator, and then a first pressure peak is detected in the pressure signal within the first pulse detection period. A second pulse detection period is set based on the window and a second heart beat time indicated by the heart beat indicator, and then a second pressure peak in the pressure signal is detected within the second pulse detection period. A determination of whether at least two pressure peaks are detected having an amplitude within the threshold amplitude range are detected prior to a time out maximum period. A blood pressure for the patient is then determined based on the pressure peaks.

One embodiment of a noninvasive blood pressure measurement system includes a blood pressure cuff comprising a pressure sensor configured to measure a pressure signal from the patient when the blood pressure cuff is inflated and a controller. The controller is configured to receive an average heart rate and/or an RR interval variability for the patient and calculate a window for pulse detection based on the average heart rate and/or the RR interval variability. A pulse detection period is set for each heart beat based on the window and a heart beat indicator indicating at least one heart beat time. The pressure signal is then examined to identify a pressure peak within each pulse detection period and a blood pressure for the patient is determined based on the pressure peaks.

Various other features, objects and advantages of the invention will be made apparent from the following description taken together with the drawings.

DETAILED DESCRIPTION OF THE DRAWINGS

Figure 1:
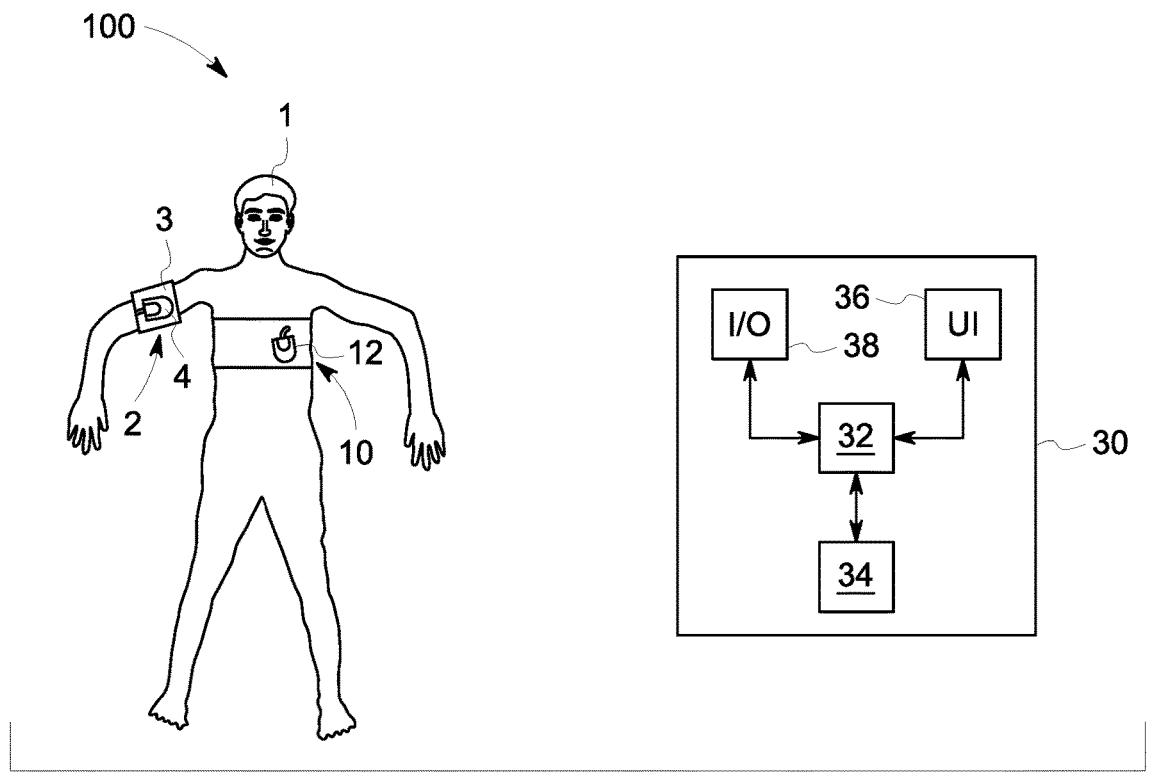
FIG. 1 is a block diagram of a patient monitoring environment including one embodiment of a noninvasive blood pressure monitor being a wireless monitor.

Non-invasive blood pressure (NIBP) monitoring systems and measurement control methods are disclosed that provides improved pressure pulse detection, including in noisy environments and without requiring prior knowledge of whether a patient has a heart condition, such as providing improved pressure pulse detection for patients with atrial fibrillation without requiring a prior diagnosis of atrial fibrillation.

A problem with prior art methods of measuring blood pressure is that blood pressure measurements can be skewed due to artifacts caused by patient motion or by the presence of arrhythmias. Many prior art oscillometric blood pressure measurement methods assume that heart beats are evenly spaced and rely on that assumption for detecting PPAs. However, where heart beats and/or stroke volumes are irregular, such assumptions are problematic.

The presence of noise further complicates the measurements by obscuring the pressure peaks in the pressure signal. The inventors have recognized that noise is particularly a problem with wireless, or "wearable," NIBP monitors that are worn by mobile patients for long periods of time wherein NIBP measurements are periodically and automatically taken without clinician oversight. The awake and mobile patient is likely to move or be in an abnormal position when the NIBP measurement is automatically triggered. Thus, the likelihood and negative impact of noise and/or disturbances in the pressure signal is higher with wearable wireless NIBP measurement systems than with traditional wired NIBP measurement systems.

Events such as these adversely affect the peak pulse amplitudes detected by the cuffs pressure sensor, resulting in erroneous blood pressure measurements. While these problems with NIBP measurements are well-recognized in the prior art, the prior art does not disclose a satisfactory method for rejecting artifacts while compensating for the presence of arrhythmias and calculating an accurate blood pressure measurement in a timely manner when arrhythmias are present.

The inventors have recognized that one problem with prior art methods and systems is that prior art methods of accurate NIBP measurement for patients with arrhythmias, such as atrial fibrillation (AFIB), require prior diagnosis or recognition of the arrhythmia prior to the start of the blood pressure measurement. This can be impractical and does not lead to sufficiently reliable and accurate NIBP detection because some arrhythmias may go undetected or undiagnosed. Additionally, this requires selection and implementation between different blood pressure detection algorithms that are particularly tailored based on diagnosis, which is cumbersome and compounds error.

In view of the foregoing problems in the relevant art recognized by the inventor, some of which are well known and long-standing, the inventor has developed the disclosed system and method that can be applied to reliably determining blood pressure in the presence of noise and regardless of arrhythmia detection or diagnosis of cardiac abnormality. As described herein, the system 100 is configured such that NIBP measurements are performed and controlled using at least one of an ECG waveform measured from the patient, a photoplethysmogram (PPG) waveform measured from the patient, or a chest impedance waveform measured from the patient. The ECG, $SpO_2$, and/or chest impedance waveforms are utilized to provide a heart beat indicator indicating at least one heart beat time, or the time at which each heart beat for the patient occurs. The chest impedance respiration signal, for instance, includes small pulsations based on the cardiac fluid changes, and such small pulsations can be used as the heart beat indicator. That heart beat time is then utilized to accurately detect the pressure pulses in the pressure signal measured by the pressure sensor in the blood pressure cuff. Thus, in one preferred embodiment, such ECG, $SpO_2$, and/or chest impedance waveforms are measured contemporaneously with pressure measurements from the pressure sensor such that they can be aligned, or correlated, in time to the oscillations in the pressure signal.

As disclosed herein, a window for pulse detection is calculated based on an average heart rate and/or an RR interval variability. The window for pulse detection specifies a length of time that can be positioned with respect to a heart beat time, or a time of a detected heart beat, within which a pulse at the NIBP measurement site should be detectable. For example, where the RR interval variability is greater than average, the window for pulse detection may be longer than average. The average heart rate and/or the RR interval variability may be received from a patient monitoring modality, such as ECG, $SpO_2$, chest impedance, or any patient monitoring device capable of obtaining such information from the patient. This may be the same modality upon which the heart beat indicator is calculated or may be from a different modality than that providing the heart beat indicator. A pulse detection period is set for each heart beat based on the window and the heart beat indicator. The pressure signal within each pulse detection period is then examined to identify a pressure peak within each pulse detection period.

Thereby, noise interference with the pressure peak identification, and thus the ultimate blood pressure measurement, can be minimized or eliminated by narrowing the periods in which the pressure signal is examined for the pressure peak based on actual heart beat measurement for the patient. The time period during which the pressure peak can be expected is accurately estimated based on the average heart rate, the RR interval variability for the patient, and the detection of an actual heart beat, based on the electrical activity of the heart. Depending on the modality of heart beat detection, the system can be configured to determine when the pulse peak at the measurement site should occur, such as when the pulse peak at the patient's arm should be detected by the cuff thereon. Where ECG is used for determining the heart beat indicator, such as based on R-peak detection for example, the pressure peak can be expected within the certain period of the heart beat occurrence.

The above-described steps are performed on the pressure signal throughout the cuff deflation process, where the blood pressure cuff is deflated in a series of pressure steps, such as according to standard cuff deflation routines. The blood pressure is then determined for the patient based on the pressure peaks, such as according to standard mean arterial pressure (MAP) systolic pressure, and/or diastolic pressure calculation and/or derivation methods examples of which are described above.

In certain embodiments, identifying the pressure peak within each pressure peak detection period includes identifying that the amplitude of the pressure peak is within a threshold amplitude range. For example, the threshold amplitude range may be configured to ensure that the pressure peaks determined at each cuff pressure step are consistent with one another. Thus, the threshold amplitude range may be determined based on an amplitude of at least one pressure peak for the patient, such as based on an average amplitude or a filtered average amplitude of a predetermined number of previous peaks. Alternatively or additionally, the threshold amplitude range determination may include comparing each pressure peak at a cuff pressure step with all previous pressure peaks measured at that cuff pressure step to determine whether any two or more pressure peaks have amplitudes that are within the threshold amplitude range of one another.

The system and method may be configured to determine whether at least two pressure peaks are detected having an amplitude within the threshold amplitude range of one another within a given cuff pressure step. In certain embodiments, a time out maximum period may be set for each cuff pressure step which may be a patient-specific value, such as calculated based on the average heart rate and/or RR interval variability for the patient or may be a predetermined value.

The disclosed blood pressure determination method may be performed contemporaneously with the blood pressure measurement to make real time measurement determinations and control the cuff pressure steps accordingly. Alternatively or additionally, the disclosed blood pressure determination methods may be performed as post-processing steps where the pressure signal is compared to the heart beat indicator and pressure peaks are detected after execution of the series of pressure steps. In the embodiments, the disclosed pulse detection period and pressure peak detection methods may be performed both as live measurement determinations and as post-processing validation methods. For example, in situations where at least two pressure pulses having amplitudes within the threshold amplitude range of one another are not detected prior to the time out maximum. At any one or more pressure steps in the live blood pressure determination, then the method may be reperformed in post processing where adjustments can be made to one or more of the alignment between the heart beat indicator and the pressure signal, the window, and/or the threshold amplitude range. The pressure signal measured from the pressure sensor in the blood pressure cuff is then processed using the window for pulse detection and the heart beat indicator.

FIG. 1 depicts one embodiment of a patient monitoring system 100 wherein a patient 1 is being monitored using a wireless NIBP monitor 2 and a wireless ECG monitor 10. The NIBP monitor 2 and the ECG monitor 10 gather the respective physiological information from the patient without requiring a physical connection to a central monitoring device or power source. Thus, the wireless monitors 2 and 10 are self-powered, such as by a battery contained therein, and may communicate physiological information of the patient, whether raw or processed physiological data, to another device or location via wireless means. In other embodiments the disclosed system may be a wired NIBP monitor and/or a wired ECG monitor wherein the patient monitoring portion of the device that does the signal processing is a bed-side device, such as may be plugged into a wall outlet for power.

Figure 2:
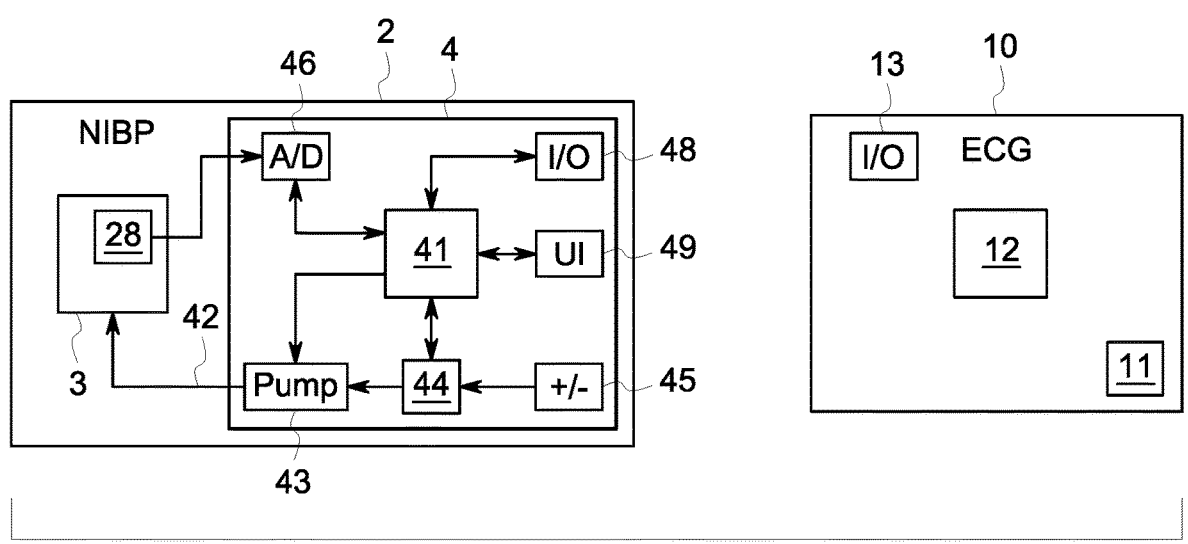
FIG. 2 is a block diagram of an exemplary noninvasive blood pressure monitor communicatively connected to an exemplary ECG monitor.

In the embodiment depicted in FIGS. 1-2, the wireless NIBP monitor 2 and the wireless ECG monitor 10 are in wireless communication with the central monitor 30. The wireless blood pressure monitor 2 has a blood pressure cuff 3 comprising a pressure sensor 28 configured to measure a cardiac pressure pulse signal from a patient's arm and a wireless blood pressure determination unit 4.

The wireless ECG monitor 10 has an ECG sensor unit 11 (which may comprise one or more ECG electrodes, electrode patches, or other elements configured to connect to the patient and obtain an electrical cardiac signal from the patient) and a wireless ECG determination unit 12 configured to process the electrical cardiac signal and provide various cardiac-related physiological information for the patient, such as heart rate and RR-interval information. The central monitor 30 has wireless transceiver 38 that communicates with the wireless transceivers of patient monitoring devices, including transceivers in wireless NIBP monitor 2 and in the wireless ECG monitor 10. Thus, the wireless transceiver 38 communicates information between the patient monitors 2 and 10 and the processing unit 32 of the central monitor 30. The wireless transceiver 38 of the monitor 30 may communicate with wireless transceivers of the respective monitoring devices 2 and 10 by any wireless means, such as via a network operating on the medical body area network (MBAN), body area network (BAN), wireless medical telemetry service (WMTS) the spectrum or on a Wi-Fi-compliant local area network (WLAN), or by Bluetooth, Bluetooth Low Energy, ZigBee, ANT, or another wireless communication standard.

In other embodiments, the patient monitoring system for the patient may include a pulse oximetry patient monitoring device (an "$SpO_2$ monitor"), which may be included as an alternative to the ECG monitor or in addition to the ECG monitor. The $SpO_2$ monitor may likewise be a wireless patient monitor with a physiological measurement unit, such as an infrared measurement device that clips to a patient's finger, and a wireless determination unit configured to receive and process signals from the sensor that communicates with the central monitor 30. Alternatively, as described above, the $SpO_2$ monitor may be part of a wired bedside patient monitoring system.

Alternatively or additionally, the patient monitoring system for the patient may include a chest impedance monitor, which may be included as an alternative to the ECG monitor or in addition to the ECG monitor. The $SpO_2$ monitor may likewise be a wireless patient monitor with a physiological measurement unit, such as a set of electrodes configured to measure impedance across a patient's chest, and a wireless determination unit configured to process the impedance signals or measurements and communicate with the central monitor 30.

In the embodiment of FIG. 1, each wireless monitoring device 2 and 10 communicates with the central monitor 30. Thus, any communication of information between the wireless monitoring devices 2 and 10 goes through the central monitor 30. However, in the embodiment of FIG. 2, the wireless NIBP monitor 2 and the wireless ECG monitor 10 may alternatively communicate directly with one another, including communicating information about the heart beat indicator, the average heart rate, the RR interval variability, or other monitoring information. Specifically, the wireless noninvasive blood pressure monitor 2 has a wireless transceiver 48 responsible for receiving input information and transmitting output information. Likewise, the wireless noninvasive ECG monitor 10 has a wireless transceiver 13 responsible for receiving input information and transmitting output information. For example, the wireless transceiver 48 of the wireless NIBP monitor 2 may communicate with the wireless transceiver 13 of the wireless ECG monitor 10 to receive the heart beat indicator, the average heart rate, the RR interval variability, or ECG information. As described above with respect to the embodiment of FIG. 1, the wireless transceivers 48 and 13 may communicate by any wireless communication standards known in the art, including MBAN, BAN, WMTS, Wi-Fi, Bluetooth, or the like.

The central monitor 30 may have a user interface 36. The user interface 36 may provide a means through which a clinician may receive or view information from the patient monitors 2 and 10 and/or to provide input to the patient monitors 2 and 10. The processing unit 32 may also be connected to a digital storage device 34 for storing the physiological data collected by the various sensor devices. The digital storage device 34 may also store processed physiological data and/or other information generated by the processor 32, and/or may operate to store other relevant patient information.

Figure 3:
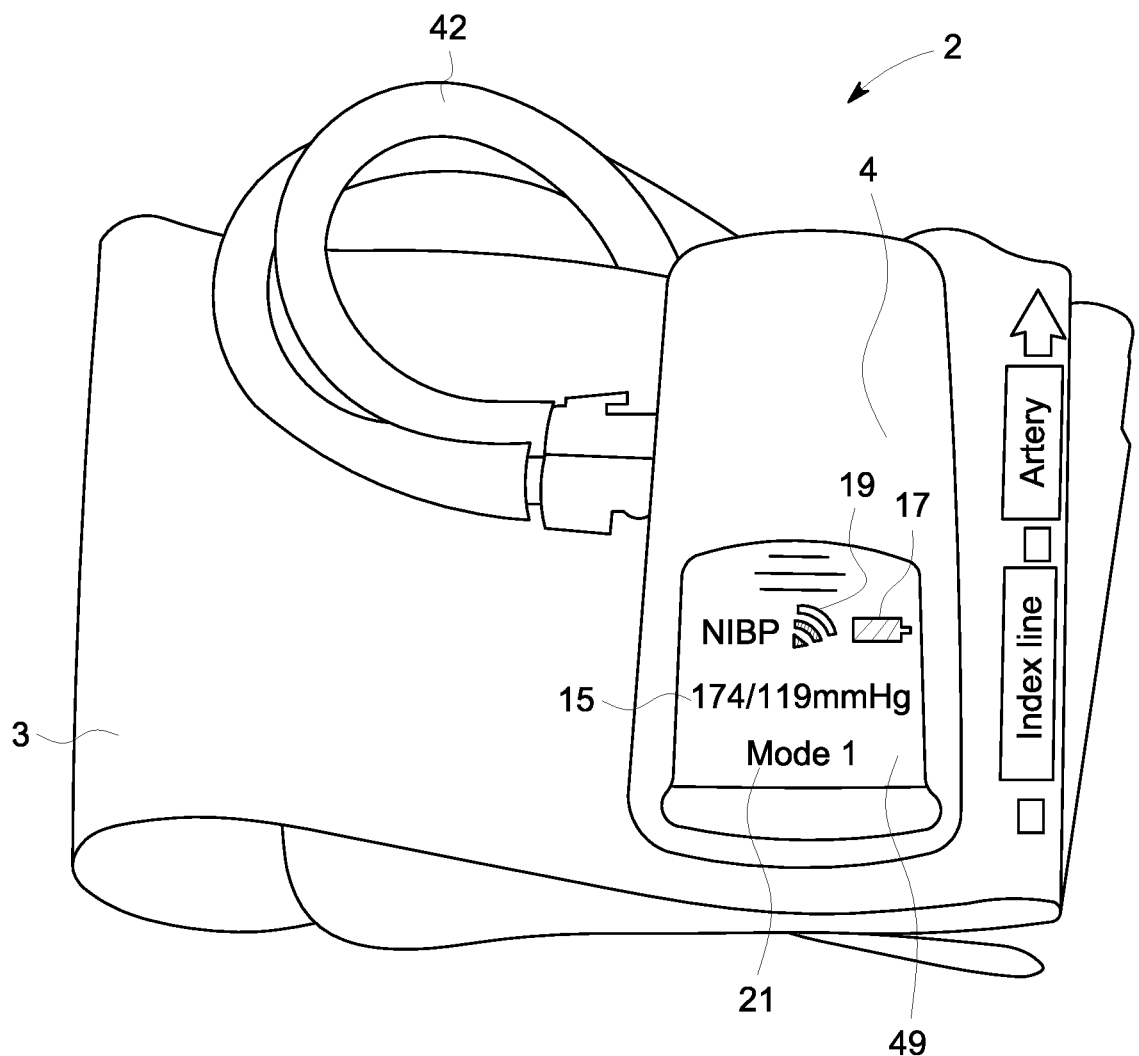
FIG. 3 depicts an exemplary embodiment of a wireless noninvasive blood pressure monitor.

The wireless NIBP monitor 2 has a blood pressure cuff 3 and a wireless blood pressure determination unit 4. As depicted in FIG. 3, the blood pressure determination unit 4 may be physically connected to the cuff 3 so that the wireless NIBP monitor 2 can easily be worn by the patient 1, such as by wrapping the cuff around the patient's arm or leg in a manner known in the art. The blood pressure determination unit 4 is configured to inflate the blood pressure cuff 3 on the patient, and to then determine a blood pressure of the patient according to the methods described herein. The blood pressure determination unit 4 may have a user interface display 49 that displays, for example, the patient's blood pressure 15 measured according to the methods disclosed herein, a battery status 17, and or a wireless connectivity status 19. The display 49 may also provide a mode indicator 21 which may indicate the mode, or method, used to calculate the patient's blood pressure 15. For example, the mode indicator 21 may indicate whether the blood pressure value for the patient is measuring using the method described herein and/or whether the heart beat indicator for the blood pressure determination is based on the ECG, $SpO_2$, and/or chest impedance waveform.

Referring again to FIG. 2, the blood pressure determination unit 4 has a pump 43 configured to inflate the blood pressure cuff 3. The pump 43 pumps air into the cuff 3 via one or more pump lines 42. The pump 43 is powered by battery 45, also housed in the blood pressure determination unit 4. The battery 45 is connected to the pump 43 through power gauge and protection module 44, which regulates the power distribution within the blood pressure determination unit 4. For example, the power from the battery 45 may be distributed via the power gauge and protection module 44 to the processor 41, analog to digital converter 46, wireless transmitter/transceiver 38, user interface 49, and pump 43. The battery 45 may be any battery capable of providing sufficient power, such as a rechargeable battery. The user interface 49 may be a display, such as shown in FIG. 3. Additionally, the user interface 49 may enable user input, such as to select a mode or to initiate a blood pressure measurement.

The wireless NIBP monitor 2 measures the patient's blood pressure by inflating the cuff 3 around the patient's arm and measuring the pressure changes in the cuff via pressure sensor 28 to measure pressure oscillations caused by blood flow in the patient's arm. Specifically, the processor 41 causes the pump 43 to inflate the cuff 3 via pump line 42. The processor 41 controls the pressure in the cuff 3 according to the methods disclosed herein to facilitate and optimize blood pressure measurement. Pressure measurements sensed by the pressure sensor 28 are transmitted to the analog-to-digital converter (A/D converter) 46, which digitizes the signals and transmits them to the processor 41. The A/D converter 46 may be any device or logic set capable of digitizing analog physiological signals. For example, the A/D converter 46 may be an analog front end (AFE).

Figure 4:
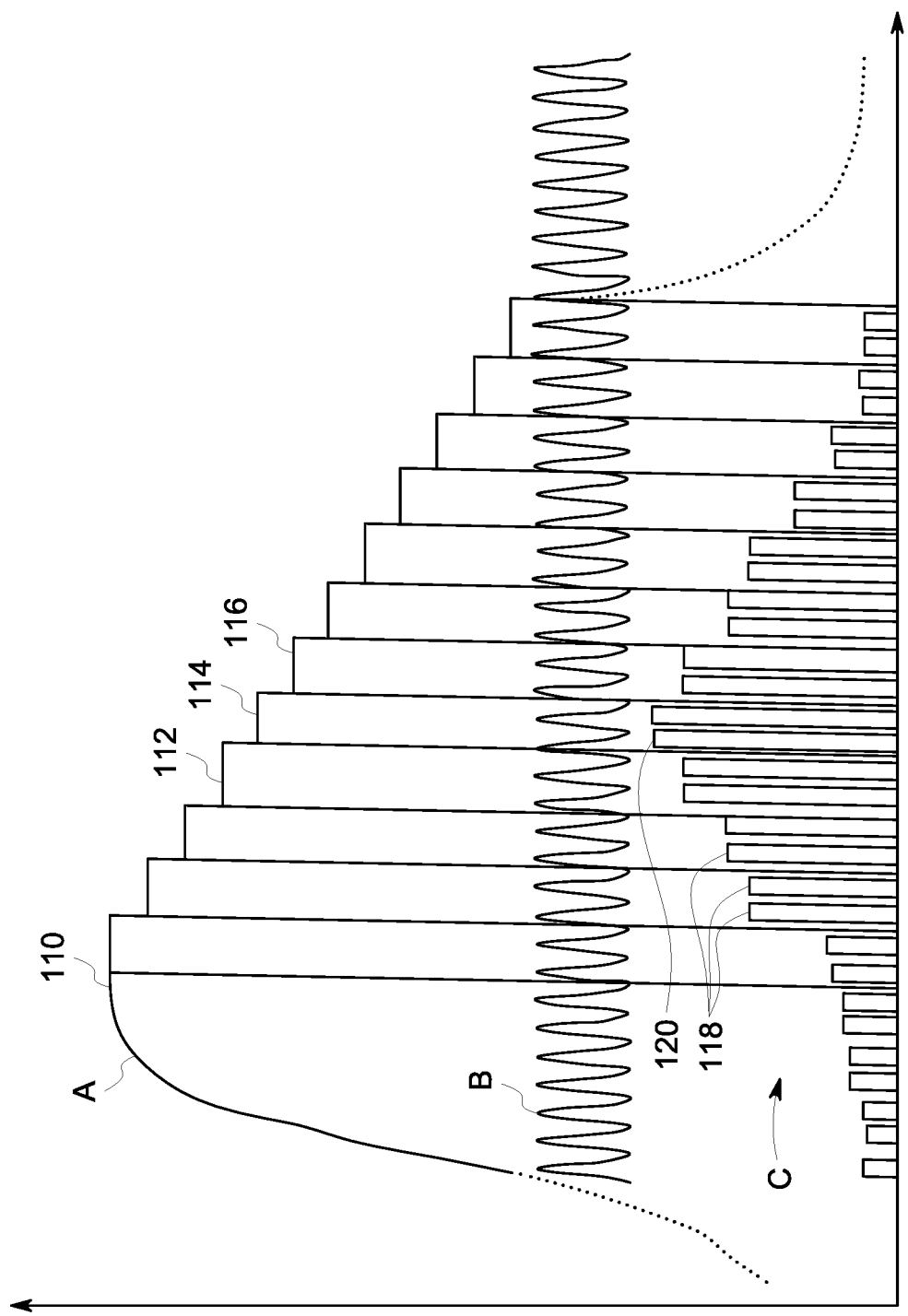
FIG. 4 is a graph showing various waveforms during an oscillometric Hood pressure measurement.

FIG. 4 shows the basic elements of measuring a patient's blood pressure using the oscillometric method. Three waveforms are shown. Waveform A represents the overall cuff pressure of the inflatable cuff illustrating a series of pressure steps, waveform B represents an ideal pressure wave showing the periodic pressure variations corresponding to the patient's pulse, and waveform (or series of measurements) C represents the measured peak pulse amplitudes for the oscillometric complexes associated with each pulse of waveform B. As can be seen, the cuff is first inflated to a maximum pressure 110, and then reduced in a series of small incremental steps such as steps 112, 114, and 116. Oscillations 118 corresponding to each pulse of the arterial waveform B are measured at each incremental cuff pressure. The PPA of the oscillations increases with each decrement of cuff pressure until the PPA reach a maximum at cuff pressure step 114. The PPA diminish with every subsequent reduction in cuff pressure. Thus, the cuff pressure at step 114 represents the patient's mean arterial pressure, and the patient's systolic and diastolic pressures can be determined therefrom.

Figure 5:
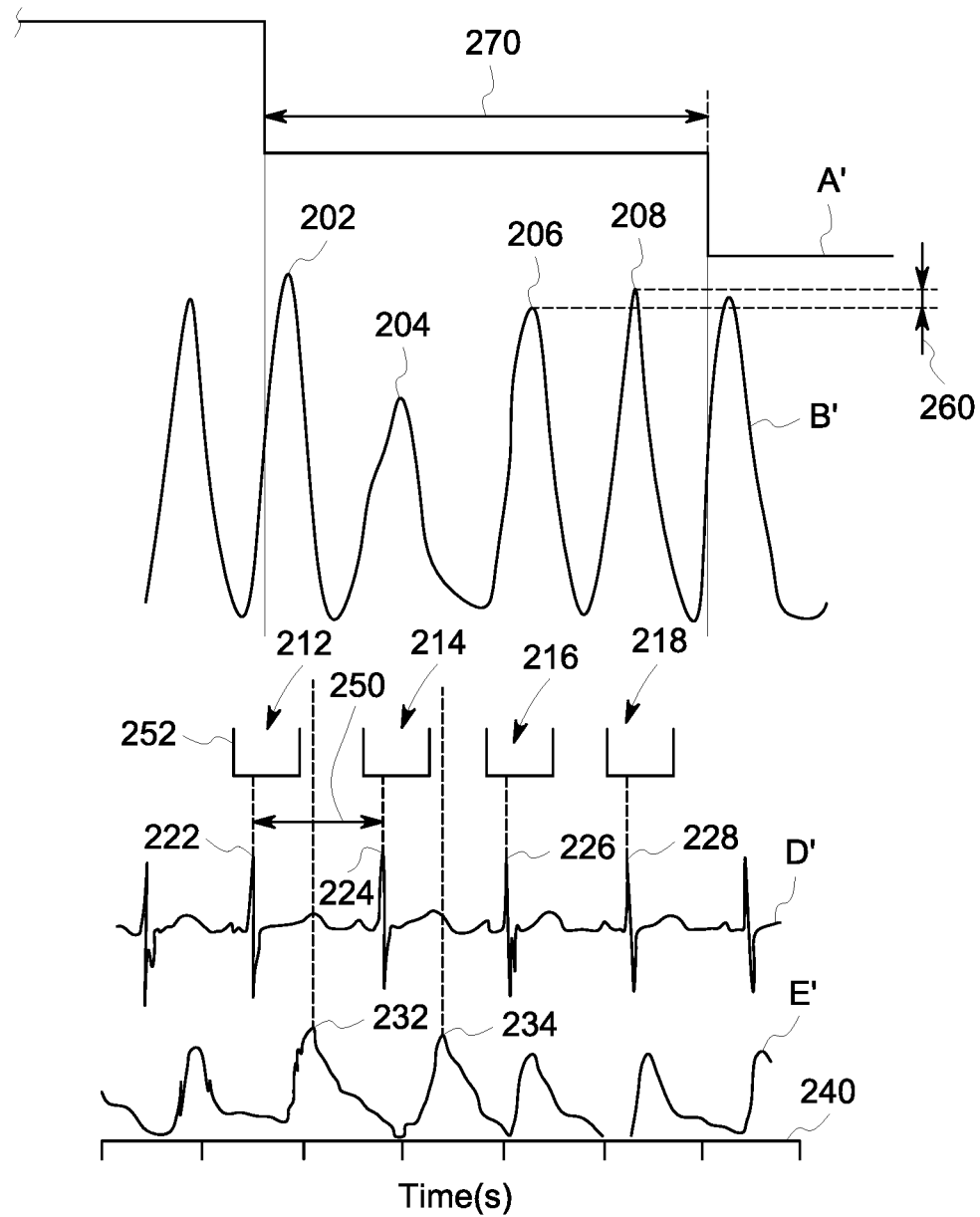
FIG. 5 is a graph showing various waveforms during an oscillometric blood pressure measurement illustrating one embodiment of measuring non-invasive blood pressure according to the present disclosure.

FIG. 5 shows a portion of cuff pressure waveform A' and a corresponding pressure signal B' measured at the blood pressure cuff. Waveform D' is the ECG waveform for the patient correlated in time with the pressure signal B'. Waveform E' is a PPG waveform for the patient correlated in time with the pressure signal B'. In various embodiments, one or the other of the ECG waveform D' or the PPG waveform E' may be utilized as the heart beat indicator.

Where the ECG waveform D' is used, any of various features of the ECG waveform may be utilized as the heart beat indicator. In one embodiment, the R-peak is utilized as the heart beat indicator, and thus the heart beat time is marked as the time at which the R-peak is detected based on the correlated time axis 240 for the various physiological signals B', D', and/or E'.

A pulse detection period for each heart beat indicated by the detected R-peaks is then set. Only the sections of the pressure signal falling within those pulse detection periods is examined for identifying a pressure peak. Thus, the pressure signal is examined only during those sections of time where a pressure peak is likely to occur, and other sections of the pressure signal falling outside of a pulse detection period can be ignored. Thereby, the influence of noise is reduced by narrowing the examination to the sections of the pressure signal where the pressure peaks are most likely to occur.

In the example at FIG. 5, each of the R-peaks 222, 224, 226, 228 in the ECG waveform D' is utilized to set each of the pulse detections periods 212, 214, 216, 218. Then, only sections of pressure signal B' occurring within one of the pulse detection periods 212, 214, 216, 218 are examined for pressure peak identification of pressure peaks 202, 204, 206, 208. The pulse detection periods 212, 214, 216, 218 are set based on the detected R-peaks 222, 224, 226, 228 and based on a known relationship between the occurrence of the heart beat indicator, here the ECG R-peak, and the relative timing of the pressure pulse at the NIBP measurement location.

In certain embodiments, that relative alignment between the pulse detection period and the detected R-peak (which could alternatively be another detected ECG waveform feature or a different identifiable feature in a different monitoring modality) may be a patient-specific determination, such as based on patient demographic data like height, weight, patient age, or the like. Alternatively, the relative alignment between the detected heart beat indicator and the respective pulse detection period may be a predetermined value based on the physiological signal and feature being utilized as heart beat indicator and the measurement location of the NIBP pressure signal.

The PPG waveform E' illustrates another exemplary heart beat indicator where the plethysmogram (PPG) waveform is depicted, such as measured using a conventional pulse oximeter sensor using infrared measurement of blood profusion at the patient's finger. Peak detection of the PPG waveform E', or PPG waveform, may be utilized as the heart beat indicator. Each pulse detection period would then be set based on the detected PPG waveform peaks. With respect to the example at FIG. 5, each of the two illustrated SpO2peaks 232 and 234 would be used to set a subsequent pulse detection period 212 and 214. The pulse detections periods 212 and 214 are set based on a predetermined relationship between the relative time occurrence of each SpO2 peak and the corresponding pressure peak at the NIBP measurement site. Where the SpO2 measurement occurs at the patient's finger and the NIBP measurement occurs at the patient's upper arm, the $SpO_2$ peak will be after the corresponding pressure peak 202, 204 measured at the patient's upper arm. Thus, in such an embodiment each pulse detection period is set as a time period prior to the PPG waveform heart beat indicator and the system looks back in time at the data collected during that window.

In other embodiments, the pulse detection period may be gated off of a different physiological signal as the heart beat indicator, such as a chest impedance waveform, an invasive blood pressure measurement, or other physiological signal from which heart beat can be reliably detected.

Each pulse detection period has a length based on a calculated window for pulse detection. Each window for pulse detection 252 has a predetermined length of time, which may be a patient-specific calculated value. For example, the window for pulse detection may be calculated based on an average heart rate for the patient and/or an RR interval variability for the patient. For example, the average heart rate and RR interval variability may be determined based on the ECG waveform D', and more particularly based on the RR intervals 250 measured therein. The RR interval variability may be calculated as a percentage, being the differences between RR interval lengths divided by the average RR interval, multiplied by 100. To provide one example, the window for pulse detection may be calculated as a percentage of the average ECG waveform period plus the RR interval variability value or some multiplier thereof. Alternatively, the window may be calculated based on the average heart rate, such as the average heart rate plus some fixed value or percentage. As another alternative, the window may be calculated based on the RR interval variability, such as a fixed value that gets increased or multiplied based on the variability number.

In an alternative embodiment, the window for pulse detection may be calculated on a beat-by-beat basis based on the pulse interval 250 for the respective heart beat period. Thus, where the heart beat interval is irregularly long or short, such as during occurrence of an arrhythmia, a corresponding window for pulse detection that is particularized to that beat length can be determined.

Once each pressure peak 202, 204, 206, 208 is detected, the respective peak is compared to a threshold amplitude range based on amplitudes of one or more other pressure peaks detected in the pressure signal B' to determine whether at least two valid pressure peaks are detected within a given cuff pressure step. Referring to the example illustrated in FIG. 5, of the four pressure peaks 202, 204, 206, 208 detected within the illustrated cuff pressure step of cuff pressure signal A', only two pressure peaks meet the threshold amplitude range requirement. Pressure peaks 206 and 208 are within a threshold amplitude range 260 of one another. Pressure peak 204 has an amplitude that is too low and pressure peak 202 that is too high, neither of which are within the threshold amplitude range of any other pressure peak within the detection period represented by the cuff pressure step.

The threshold amplitude range may be a predetermined value or may be a patient-specific value calculated based on the pressure signal B', the ECG signal D', or some other physiological measurement for the patient. For example, the patient-specific threshold amplitude range may be calculated based on an average pressure peak amplitude variability for the patient. Such a patient-specific threshold amplitude range may be more feasibly calculated in a post-processing scenario where the pressure signal for the entire blood pressure measurement cycle is available.

A time out maximum period may be set for each cuff pressure step, which is the maximum time that each cuff pressure step in the series of pressure steps is maintained. This also then sets the duration during which at least two pressure peaks must be detected that meet the threshold amplitude range requirement. In FIG. 5, the time out maximum period 270 is equal to the amount of time that the respective cuff pressure step is maintained. In certain embodiments, each cuff pressure step is maintained for the time out maximum period, and thus all cuff pressure steps in the series of pressure steps are maintained for the same duration of time.

In other embodiments, the cuff pressure may be controlled based on the detected pressure peaks such that the system can progress to the next pressure step once two pressure peaks meeting the pressure amplitude range requirement are detected. This has the benefit of potentially decreasing the total duration of the blood pressure measurement cycle by decreasing the duration of one or more of the cuff pressure step durations.

Figure 6:
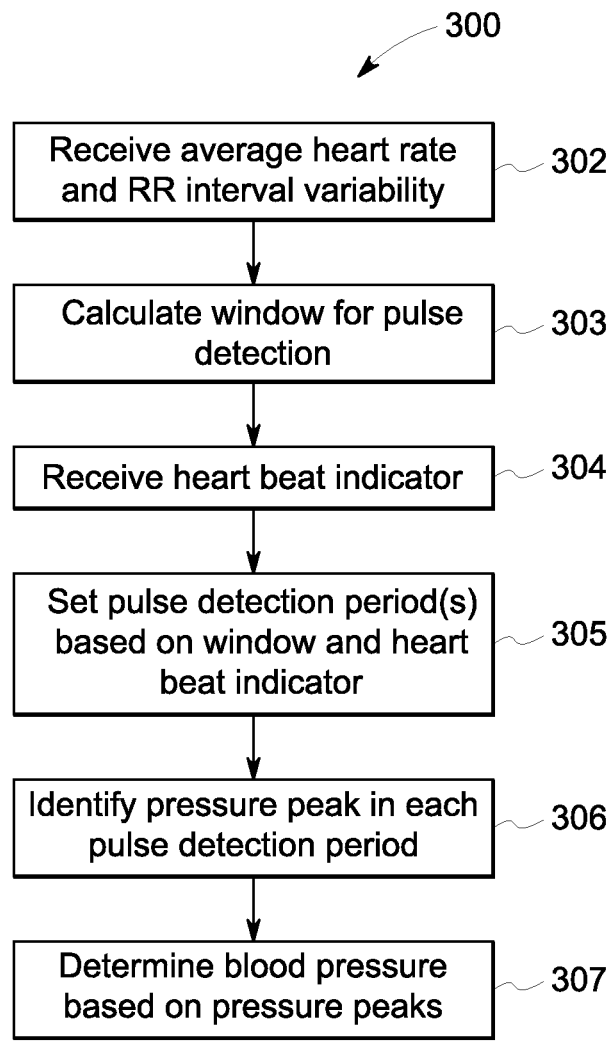
FIGS. 6-8 ae flow charts depicting methods, or portions thereof, of detecting non-invasive blood pressure according to the present disclosure.
Figure 7:
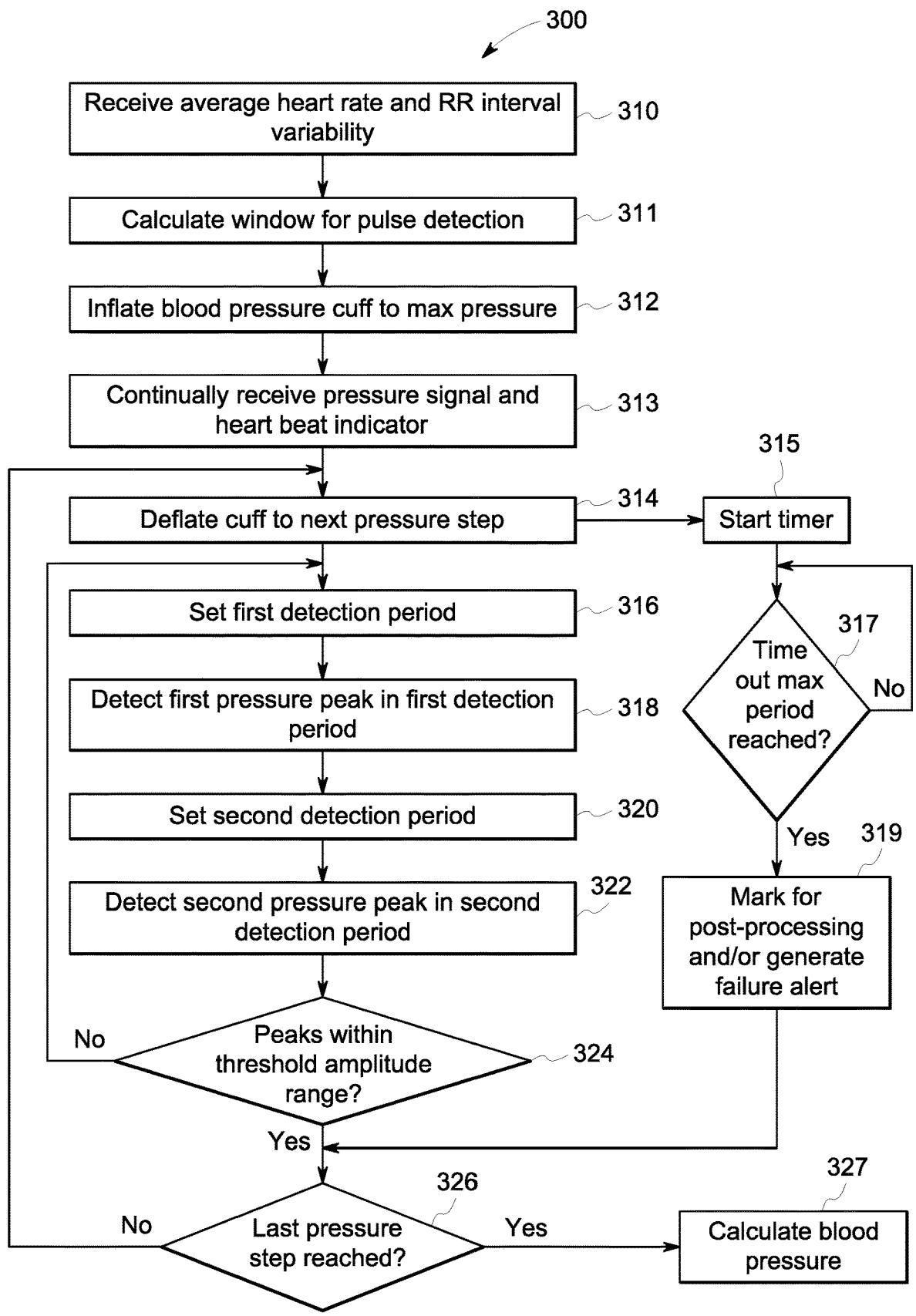
Figure 8:
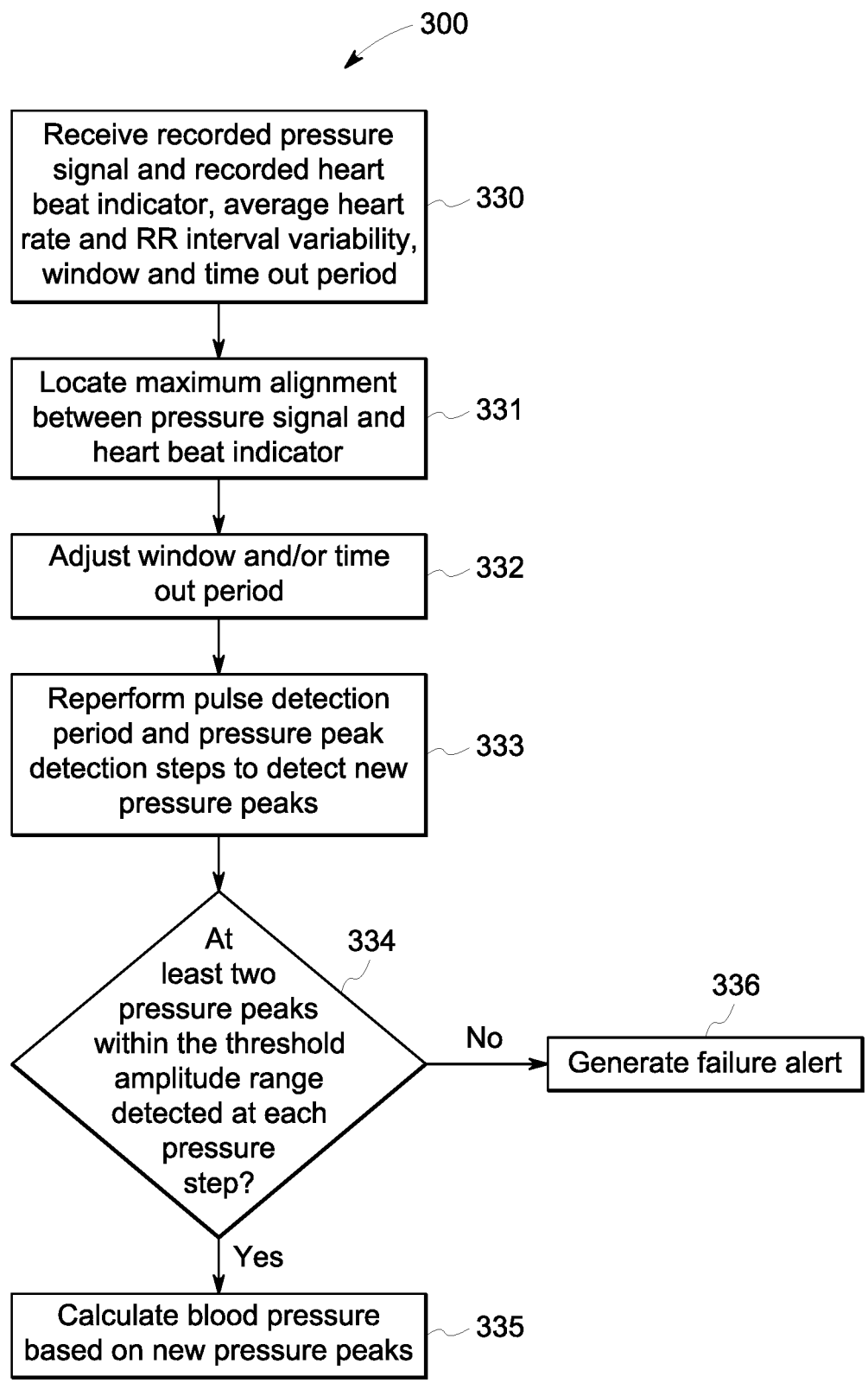

FIGS. 6-8 are flowcharts depicting methods 300, or portions thereof, of detecting noninvasive blood pressure according to the present disclosure. The methods may be carried out by one or more controllers within the system 100, such as by algorithms stored and executed within the determination unit 4 of the blood pressure monitor 2 and/or by algorithms stored in storage 34 of the central monitor 30 and executed on the processor 32.

An average heart rate and RR interval variability are received at step 302 and a window for pulse detection is calculated at step 303. The heart beat indicator is received at step 304 and the pulse detection period(s) is set at step 305 based on the window and the heart beat indicator. A pressure peak is then identified in each pulse detection period at step 306 by examining the pressure signal within that pulse detection period. Once the relevant pressure peaks have been detected, the blood pressure is determined based thereon at step 307, such as according to conventional methods described above.

FIG. 7 illustrates another embodiment of a method 300 of measuring noninvasive blood pressure, which is a real time, live calculation performed during the blood pressure measurement. An average heart rate and RR interval variability for the patient is received at step 310 and the window for pulse detection is calculated at step 311. The blood pressure cuff is inflated to max pressure at step 312 and the pressure signal is received at step 313 from the pressure sensor within the blood pressure cuff, along with receipt of the heart beat indicator. Preferably, the pressure signal and heart beat indicator are correlated in time according to a single time axis, as described above.

The blood pressure cuff is then deflated in a series of pressure steps, where the disclosed pressure peak detection methods are performed at each cuff pressure step. When the cuff is deflated to the next pressure step, represented at step 314, a timer is started at step 315 such that the time out maximum period can be monitored. If the time out maximum period is reached prior to detection of two pressure peaks in the threshold amplitude range, illustrated at step 317, then the measurement is marked for post-processing at step 319. Alternatively or additionally, a failure alert may be generated indicating to the clinician and/or a marking in the patient record along with the blood pressure measurement that an insufficient number of pressure peaks were detected for one or more of the cuff pressure steps.

Meanwhile, steps are executed for detecting pressure peaks. A first detection period is set at step 316 and the pressure signal within the first pulse detection period is examined at step 318 to identify a first pressure pulse. Once a second heart beat time is indicated by the heart beat indicator, then a second pulse detection period is set at step 320. The pressure signal within the second pulse detection period is then examined at step 322 to detect a second pressure peak. Step 324 is then executed to determine whether the first and second pressure peaks are within the threshold amplitude range of one another. If so, then two pressure peaks have been successfully detected and the requirement has been met for the respective cuff pressure step.

If the threshold amplitude range is not met at step 324, then the pulse detection period and pressure peak detection steps are re-executed until either the time out maximum period is reached or two peaks meeting the threshold amplitude range requirement are detected. In the depicted example, the cuff pressure is automatically decreased once two pressure peaks meeting the threshold amplitude range requirement are met. Thus, if the last pressure step has not been reached at step 326, then the process returns to step 314 to deflate the blood pressure cuff to the next pressure step in the series of pressure steps. In other embodiments (particularly where post-processing may be implemented as described herein), each cuff pressure step may automatically be maintained for the time out maximum period regardless of whether two pressure peaks meeting the threshold amplitude range requirement are detected.

Once the last pressure step in the series of pressure steps is reached and the peak detection process has occurred for the last pressure step, then the blood pressure is calculated at step 327.

FIG. 8 depicts a method of measuring noninvasive blood pressure involving the disclosed pressure peak detection algorithm implemented in a post-processing setting. The recorded pressure signal and record heart beat indicator are received at step 330, which includes the waveforms for the entirety of the blood pressure measurement process across the series of pressure steps. The average heart rate and RR interval variability may also be provided, as well as the calculated window and time out period that may have been calculated during any real-time blood pressure measurement process.

Maximum alignment between pressure signal and the heart beat indicator is then located at step 331. Maximum alignment may be reached where the largest number of pulse peaks meeting the threshold amplitude range requirement correlate with the relevant heart beat indicator, such as the R-peaks or the SpO2peaks. The window and/or the time out period may also be adjusted at step 332. For instance, the window for pulse detection may be adjusted based on each RR interval. Alternatively or additionally, each time out maximum period may be adjusted from the value used during real time processing. For example, a fixed time out maximum period may be utilized during the real time processing algorithm, and then a patient-specific time out maximum period may be calculated for post-processing.

The pulse detection period and pressure peak detection steps are then re-performed at step 333 in the post-processing context to detect new pressure peaks. The new pressure peaks are then examined to determine whether at least two of them meet the threshold amplitude range requirements are detected at each pressure step, as presented at step 334. If so, then a blood pressure is calculated for the patient based on the new pressure peaks. If not, then a failure alert is generated at step 336, which at certain embodiments may trigger re-measurement of the noninvasive blood pressure using the blood pressure cuff.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A method of measuring non-invasive blood pressure, the method comprising:
   determining, at a controller, a window for pulse detection for a patient;
   receiving, at the controller, a pressure signal measured from a pressure sensor in a blood pressure cuff;
   setting, with the controller, a pulse detection period for each heart beat based on the window, a heart beat indicator indicating at least one heart beat time, and an RR interval variability;
   examining, at the controller, the pressure signal within each pulse detection period to identify a pressure peak therein;
   controlling, with the controller, a pressure of the blood pressure cuff to maintain each of a series of cuff pressures until at least two pressure peaks are identified having an amplitude within a threshold amplitude range within each of the series of cuff pressures; and
   determining, at the controller, a blood pressure for the patient based on the pressure peaks.

2. The method of claim 1, further comprising:

calculating the window for pulse detection based on an average heart rate and/or the RR interval variability for the patient; and determining the heart beat indicator based on at least one of an ECG waveform for the patient, photoplethysmogram waveform for the patient, or a chest impedance waveform for the patient.

3. The method of claim 2, wherein the heart beat indicator is determined based on detected R-peaks in the ECG waveform for the patient.

4. The method of claim 1, further comprising determining the threshold amplitude range based on an amplitude of at least one previous pressure peak for the patient.

5. The method of claim 1, further comprising:

calculating a time out maximum period based on an average heart rate and/or the RR interval variability; and controlling the pressure of the blood pressure cuff to maintain each of the series of cuff pressures until either the at least two pressure peaks within the threshold amplitude range are identified or the time out maximum period has expired.

6. A method of measuring non-invasive blood pressure using a blood pressure cuff, the method comprising:

receiving an average heart rate and an RR interval variability for a patient;

calculating a window for pulse detection based on the average heart rate and the RR interval variability;

receiving a pressure signal measured from a pressure sensor in the blood pressure cuff;

receiving a heart beat indicator indicating heart beat times for the patient;

deflating the blood pressure cuff in a series of pressure steps and at each pressure step:

(a) setting a first pulse detection period based on the window and a first heart beat time indicated by the heart beat indicator;

(b) detecting a first pressure peak in the pressure signal within the first pulse detection period;

(c) setting a second pulse detection period based on the window and a second heart beat time indicated by the heart beat indicator;

(d) detecting a second pressure peak in the pressure signal within the second pulse detection period;

(e) continuing to set pulse detection periods and detect pressure peaks until at least two pressure peaks are detected having an amplitude within a threshold amplitude range prior to a time out maximum period;

(f) controlling deflation of the cuff to a next pressure step in the series of pressure steps; and determining a blood pressure for the patient based on the at least two pressure peaks at each pressure step.

7. The method of claim 6, wherein when the at least two pressure peaks having the amplitude within the threshold amplitude range are not detected prior to the time out maximum period at any one or more pressure steps in the series of pressure steps, then adjusting the threshold amplitude range and reperforming steps (a) through (f) using the pressure signal and the heart beat indicator recorded during the series of pressure steps and then redetermining the blood pressure for the patient based on the at least two pressure peaks at each pressure step.

8. The method of claim 6, wherein when the at least two pressure peaks having the amplitude within the threshold amplitude range are not detected prior to the time out maximum period at any one or more pressure steps in the series of pressure steps, then adjusting the window and reperforming steps (a) through (f) using the pressure signal and the heart beat indicator recorded during the series of pressure steps and then redetermining the blood pressure for the patient based on the at least two pressure peaks at each pressure step.

9. The method of claim 6, wherein when the at least two pressure peaks having the amplitude within the threshold amplitude range are not detected prior to the time out maximum period at any one or more pressure steps in the series of pressure steps, then adjusting the threshold amplitude range and adjusting the window and reperforming steps (a) through (e) using the pressure signal and the heart beat indicator recorded during the series of pressure steps and then redetermining the blood pressure for the patient based on the at least two pressure peaks at each pressure step.

10. The method of claim 6, wherein when the at least two pressure peaks having the amplitude within the threshold amplitude range are not detected prior to the time out maximum period at any one or more pressure steps in the series of pressure steps, then:

reinflating the blood pressure cuff;

deflating the blood pressure cuff in the series of pressure steps and at each pressure step performing steps (a) through (f).

11. The method of claim 6, further comprising calculating the time out maximum period based on the average heart rate and the RR interval variability.

12. The method of claim 6, further comprising determining the threshold amplitude range based on an amplitude of at least one previous pressure peak for the patient.

13. The method of claim 6, further comprising determining the heart beat indicator based on at least one of an ECG waveform for the patient, photoplethysmogram waveform for the patient, or a chest impedance waveform for the patient.

14. A non-invasive blood pressure measurement system comprising:

a blood pressure cuff comprising a pressure sensor configured to measure a pressure signal from a patient;

a controller configured to:

receive an RR interval variability for a patient;

calculate a window for pulse detection based on the RR interval variability;

set a pulse detection period for each heart beat based on the window and a heart beat indicator indicating at least one heart beat time;

examine the pressure signal to identify a pressure peak within each pulse detection period;

controlling a pressure of the blood pressure cuff to maintain each of a series of cuff pressures until at least two pressure peaks are identified having an amplitude within a threshold amplitude range within each of the series of cuff pressures; and determine a blood pressure for the patient based on the pressure peaks.

15. The system of claim 14, wherein the controller is further configured to control deflation of the pressure cuff in a series of pressure steps based on the pressure peaks.

16. The system of claim 15, wherein the controller is further configured to:

calculate a time out maximum period based on an average heart rate for the patient and the RR interval variability; and control the deflation of the blood pressure cuff to maintain each of the series of cuff pressures until either the at least two pressure peaks within the threshold amplitude range are identified or the time out maximum period has expired.

17. The system of claim 14, wherein the heart beat indicator is determined based on detected R-peaks in an ECG waveform for the patient.

18. The system of claim 14, wherein the controller is further configured to:
determine the threshold amplitude range based on an amplitude of at least one previous pressure peak for the patient.

19. The system of claim 18, wherein the controller is further configured to:
determine whether the at least two pressure peaks are detected having the amplitude within the threshold amplitude range prior to a time out maximum period;
if the at least two pressure peaks having the amplitude within the threshold amplitude range are not detected prior to the time out maximum period at any one or more pressure steps in a series of pressure steps, then adjust the threshold amplitude range and/or adjust the window and re-examine the pressure signal within each of the pulse detection periods to identify a new pressure peak within each pulse detection period and determine the blood pressure for the patient based on the new pressure peaks; and
if the at least two pressure peaks having the amplitude within the threshold amplitude range are detected prior to the time out maximum period at any one or more pressure steps in a series of pressure steps, then determine the blood pressure for the patient based on the at least two pressure peaks.

* * * * *